United States Patent [19]
Mueller et al.

[11] Patent Number: 5,272,178
[45] Date of Patent: Dec. 21, 1993

[54] COMPOUNDS OF CYCLIC PHENOLIC THIOETHERS WHICH ARE USEFUL IN STIMULATING AND INHIBITING SUPEROXIDE GENERATION

[75] Inventors: Richard A. Mueller, Glencoe; Richard A. Partis, Evanston, both of Ill.

[73] Assignee: G. D. Searle & Co., Chicago, Ill.

[21] Appl. No.: 45,449

[22] Filed: Apr. 8, 1993

Related U.S. Application Data

[63] Continuation of Ser. No. 794,759, Nov. 18, 1991, abandoned.

[51] Int. Cl.$^5$ .................. A61K 31/095; C07C 323/17
[52] U.S. Cl. .................. 514/570; 514/530; 514/532; 514/571; 514/618; 514/679; 514/699; 560/11; 560/15; 560/17; 562/426; 562/429; 562/431; 564/162; 568/31; 568/37; 568/42; 568/43; 568/75
[58] Field of Search .............. 514/530, 532, 570, 571, 514/618, 679, 699; 560/11, 15, 17; 562/426, 429, 431; 564/162; 568/31, 37, 42, 43, 75

[56] References Cited

U.S. PATENT DOCUMENTS

| | | | |
|---|---|---|---|
| 3,574,512 | 4/1971 | Weber et al. | 549/51 |
| 4,029,812 | 6/1977 | Wagner et al. | 424/324 |
| 4,076,841 | 2/1978 | Wagner et al. | 424/324 |
| 4,078,084 | 3/1978 | Wagner et al. | 424/324 |
| 4,153,803 | 5/1979 | Thiele et al. | 560/57 |
| 4,621,098 | 11/1986 | Umminger et al. | 514/562 |
| 4,711,903 | 12/1987 | Mueller et al. | 514/318 |
| 4,755,524 | 7/1988 | Mueller et al. | 514/318 |
| 4,801,611 | 1/1989 | Chinn et al. | 514/532 |
| 5,064,860 | 11/1991 | Mueller et al. | 514/568 |
| 5,082,854 | 1/1992 | Mueller et al. | 514/537 |
| 5,147,893 | 9/1992 | Mueller et al. | 514/530 |

FOREIGN PATENT DOCUMENTS

| | | | |
|---|---|---|---|
| 0131221 | 1/1985 | European Pat. Off. | 514/562 |
| 0293900 | 12/1988 | European Pat. Off. | 514/562 |
| 0512559A1 | 11/1992 | European Pat. Off. | 514/562 |
| 49-116035 | 11/1974 | Japan | 514/562 |
| 4-69375 | 3/1992 | Japan | 560/11 |

OTHER PUBLICATIONS

Auer, D. E. et al., *J. Vet. Pharmacol. Therap.*, 13(1):59–66 (1990).
Beiemond, P., et al., *Scand J. Rheumatology*, 19: 151–156 (1990).
Caglioti, et al., "Acid Decomposition of Tosylazocyclohex-1-ene and 3-Tosylazocholesta-3,5-diene," *J. Org. Chem.*, 38(5):920–923, 1972.

(List continued on next page.)

Primary Examiner—C. Warren Ivy
Assistant Examiner—Zinna N. Davis
Attorney, Agent, or Firm—Roberta L. Hastreiter; Roger A. Williams

[57] ABSTRACT

The present invention relates to compounds of the formula:

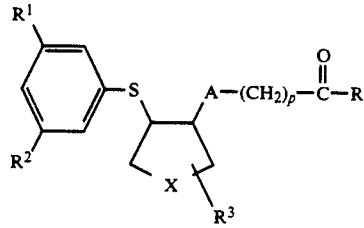

wherein $R^1$ and $R^2$ are the same or different and independently represent tert-alkyl, phenyl, or hydrogen; $R^3$ represents hydrogen or alkyl; X represents O, S or $(CH_2)_m$ wherein m is 1 or 2; A represents O or $S(O)_n$ wherein n is 0, 1, or 2; p is an integer from 0 to 4; and R represents alkyl; OH; $OR^4$ wherein $R^4$ is alkyl; or $NR^5R^6$ wherein $R^5$ is hydrogen or alkyl, and $R^6$ is hydrogen, alkyl, heterocyclealkyl, substituted heterocyclealkyl, cycloalkyl, substituted cycloalkyl, phenyl, substituted phenyl, phenylalkyl, or substituted phenylalkyl, or $NR^5R^6$ together form a heterocyclic ring which may optionally be substituted; or $(CH_2)_tCOOR^7$ wherein t is an integer from 1 to 4 and $R^7$ is hydrogen or alkyl; and the pharmaceutically acceptable salts thereof. The compounds are inhibitors or stimulators of superoxide generation.

18 Claims, No Drawings

OTHER PUBLICATIONS

Cencetti, M., et al., *Clinincal Rheumatology*, 9(1):51-55 (1990).

Cross, C. E., et al., *Ann. Int. Med.*, 107:526-545 (1987).

Davis, F. A., et al., "Chemistry of the Sulfur-Nitrogen Bond. VII. Rearrangement of Sulfenimines (S-Aryl Thiooximes) to Beta-Keto Sulfides. Attempted Synthesis of Benzo[b]thiophenes," *J. Org. Chem.*, 39(6): 807-809 (1974).

Kal'Yan, et al., *Izv. Akad Mauk SSSR Ser Kim*, 2:378-86 (1982).

Kanai, Kenichi, CA 107:197783q (1CB7).

Katayama, K., et al., *Agents and Actions*, 21(3/4): 269-271 (1987).

Kanofsky, J. R., *Chem. Biol. Interactions*, 70:1-28(1989).

Katsumi, Ikuo, "Studies on Styrene Derivatives," *Chem. Pharm. Bull.*, 34(4):1619-1627 (1986).

Kocan, G. et al, Inflammation Research Association, Fifth International Conference Poster Session, Abstract 20, Sep. 23-27, 1990.

Kreutner, W., et al., *J. Pharmacol. Exp. Ther.*, 247(3):997-1003 (1988).

Kukreja, R., et al., *Circulation Research*, 59 (6): 612-619 (1986).

MacKenzie, N. E., et al., "Ring Contractions of Thiochroman-4-ones and Thiochromen-4-ones," *J. Chem. Soc. Perkin Trans.* 1(2):395-402, 1981.

Medvedev, A., et al., *Khimiya i Khimicheskaya Tekhnologiya*, 20, pp. 568-675 (1977).

Magerramov, et al., "Reactions to Arenesulfenyl Chlorides with Methylenecycloalkanes and Vinylcyclopropane," *Zh. Organ. Khim*, 26(11): 2333-41 (1990).

Mukaiyama, T., et al., "Reactions of Mercuric Salts with Bis(diethylthiocarbamoyl) Disulfide and Benzenesulfenyl Chloride," *J. Org. Chem.* 33(6): 2242-5 (1968).

Pushkin, et al., "Doping Effect and Acid Catalysis in the Addition of Sulfonyl Chlorides to Cyclohexene in Acetic Acid," *Zh. Organ. Khim.*, 27:(7):1473-8 (1991).

Shepherd, V. L., *Semin. Respir. Infect.* (United States) Jun. 1986, 1(2), pp. 99-106.

Trost, B. M., et al. "Hydroxysulfenylation of Olefins. An Olefin Cleavage with Functional Group Differentiation," *Journal of the American Chemical Society*, 100(22):7103-7106, Oct. 25, 1978.

Ward, P. A., et al., *Free Radical Biology & Medicine*, 5:403-408 (1988).

Youn, J. H., et al. "Synthesis of Enantiomerically Enriched α-Sulfenylated Keytones and Aldehydes," *Synthesis—Journal of Synthetic Organic Chemistry*, (2):159-161, Feb. 1987.

Zefirov, et al., "A New Method of Increasing the Effective Electrophilicity of Weak Electrophiles", p. 223.

Zefirov, N. S., et al., "Stereochemical Studies—XX Conformations of 1,2-Trans-Disubstituted Cyclohexanes," 1976. *Tetrahedron*, 32:1211-1219 (1976).

Chemical Abstracts, vol. 77, No. 7, Abstract 61,306r, Aug. 14, 1972.

COMPOUNDS OF CYCLIC PHENOLIC THIOETHERS WHICH ARE USEFUL IN STIMULATING AND INHIBITING SUPEROXIDE GENERATION

This is a continuation of application Ser. No. 07/794,759, filed Nov. 18, 1991, now abandoned.

BACKGROUND OF THE INVENTION

1. Field of the Invention

The present invention relates to cyclic phenolic thioethers and more particularly relates to the novel compounds of Formula I which are inhibitors or stimulators of superoxide generation and may also inhibit cyclooxygenase or 5-lipoxygenase. The compounds of the present invention which stimulate superoxide generation may be useful as adjunctive therapeutic agents in the treatment of infections. Other compounds of the present invention which inhibit superoxide generation may be useful in the therapeutic or prophylactic treatment of disease conditions which are mediated wholly or partly by superoxide generation such as adult respiratory distress syndrome, superoxide mediated inflammatory or allergic conditions, and other medical conditions which are caused by or aggravated by superoxide.

The compounds of Formula I which inhibit cyclooxygenase or 5-lipoxygenase are useful, for example, as anti-inflammatory and/or anti-allergy agents and in the treatment of hypersensitivity reactions, psoriasis, asthma, and related disorders and conditions in which physiologically active agents formed in the arachidonic acid metabolic pathway are involved. Compounds of the present invention may be useful in treating inflammatory and allergic conditions such as arthritis, asthma, and psoriasis.

2. Background Information

Recently, oxygen radicals have been implicated in the pathogenesis of many diseases. This implication is reflected by the many conferences devoted to this topic, books on the subject of free radicals and disease, and the appearance of two new specialized journals: *Free Radical Research Communications*, and *Free Radical Biology and Medicine*.

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," ANN. INT. MED., 107:526-545 (1987) (see Table 1, p. 527) and Ward, P. A., et al., "Oxygen Radicals, Inflammation, and Tissue Injury," FREE RADICAL BIOLOGY & MEDICINE, 5:403-408 (1988). Among the clinical conditions in which oxygen radicals are thought to be involved are, for example, inflammatory-immune injury, autoimmune diseases, ischemia-reflow states, aging disorders, cancer, cigarette-smoke effects, emphysema, acute respiratory distress syndrome (ARDS), atherosclerosis, rheumatoid arthritis, senile dementia, cataractogenesis, retinopathy of prematurity, radiation injury and contact dermatitis.

Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells such as neutrophils, monocytes and macrophages, eosinophils, and endothelial cells; and antioxidation reactions; and exogenous, such as redox-cycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Those compounds of the present invention which inhibit superoxide generation may be useful in the treatment of diseases mediated by superoxide generation.

There are also some conditions in which the generation of superoxide may be desirable. Those compounds of the present invention which stimulate superoxide generation may be useful in the adjunctive therapy of microbial infections. See Goodman and Gilman's, The Pharmacological Basis of Therapeutics (7th Edition, 1985) p. 660-673; P. A. Ward, et. al., "Oxygen Radicals, Inflammation and Tissue Injury," FREE RADICAL BIOLOGY & MEDICINE, 5: 403-408 (1988); and C. E. Cross, et. al., "Oxygen Radicals and Human Disease,"; ANN. INT. MED., 107: 526-545 (1987). Generation of reactive oxygen species is a critical event in successful host defense against invading organisms. Both neutrophils and macrophages rely on a variety of oxidants to damage bacterial constituents (see V. L. Shepherd, "The role of the respiratory burst of phagocytes in host defense," SEMIN. RESPIR. INFECT. (United States) Jun. 1986, 1(2) p. 99-106.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects.

Those compounds of the present invention which inhibit cyclooxygenase inhibit the synthesis of prostaglandins via the cyclooxygenase pathway of arachidonic acid metabolism. These prostaglandin synthetase inhibitors may exhibit anti-inflammatory, anti-pyretic and analgesic activity, and are useful in the treatment of inflammatory conditions such as arthritis.

The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. LTB4 may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. LTB4 is not only chemotactic for neutrophils and monocytes, but is also highly active in stimulating eosinophil locomotion. LTB4 also stimulates calcium influx and aggregation of polymorphonuclear leukocytes and LTB4 may, thus, play an important role in mediating both acute and chronic inflammation.

Rheumatoid spondylitis is characterized by an acute neutrophil flareup in the joint which is associated with elevated levels of LTB4. LTB4 is also present in gouty effusions; and exposure to urate crystals is known to stimulate LTB4 production by neutrophils. Accordingly, those compounds of the present invention which inhibit 5-lipoxygenase through inhibition of neutrophil attraction and activation in arthritic joints should reduce the protease and oxidative burden believed responsible for joint destruction in arthritic diseases.

Prior to the recognition of the significance of the arachidonic acid metabolism pathway in allergic reactions and inflammation, the search for effective therapeutic agents was based primarily on those agents which treated the symptoms of allergy and inflammation. There has since been an effort to develop new drugs which selectively block the formation of the mediators of these conditions, and the present invention provides new chemical entities which are inhibitors of the arachidonic acid pathway and are useful in the treatment of asthma, rheumatoid arthritis, psoriasis, and other allergic, hypersensitivity, and inflammatory conditions.

Various thioether compounds have been described previously. For example, U.S. Pat. No. 4,711,903 and its continuation-in-part, 4,755,524 disclose compounds of the formula

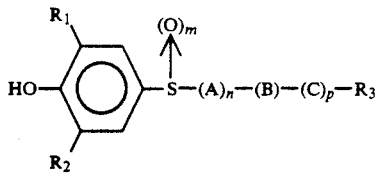

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; and the pharmaceutically acceptable salts thereof. The compounds are specific inhibitors of 5-lipoxygenase and are useful in the treatment of local and systematic inflammation, allergy and hypersensitivity reactions and other disorders in which agents formed in the 5-lipoxygenase metabolic pathway are involved.

U.S. Pat. No. 4,621,098 and its equivalent, European Patent Application Publication No. 0131221 discloses compounds of the formula

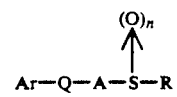

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene, and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0 without mention of any preference among the numerous possible substituents for R or substituted phenyl as Ar. In contrast to the invention disclosed in the foregoing publication, the compounds of the present invention all have cycloalkyl at the position corresponding to A as well as having di(tertiary)-alkyl or diphenyl groups as substituents on the phenol moiety corresponding to the substituted Ar group in the above publication which, as described therein, may or may not comprise a phenol.

U.S. Pat. Nos. 4,029,812, 4,076,841 and 4,078,084 disclose compounds of the formula

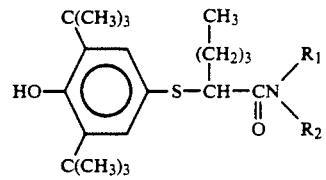

comprising 2-(3,5-di-tert -butyl-4-hydroxy-phenyl) thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tertbutyl-4-hydroxythiophenol, and hydrogen sulfide to acrylate derivatives have been described. See Medvedev et al., Khimiya; Khimicheskaya Tekhnologiya, Volume 20, (1977), pp. 568-574. The compounds resulting from the foregoing process have the general formulas $RS(CH_2)_nX$ and $S(CH_2CH_2X)_2$ in which R is 3,5-di-tert-butyl-4-hydroxyphenyl and X represents, for example, —C≡N, $NH_2$, $CH(OH)CH_2Cl$, OH, COCl and various carboxy, carboxylate and amide functions. Compounds of formula I according to the present invention or 5-lipoxygenase activity for structurally related compounds are not disclosed.

U.S. Pat. No. 4,153,803 discloses cholesterol-lowering phenoxyalkanoic acid esters of the formula

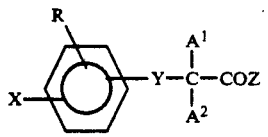

wherein, when Y is sulfur, X is hydrogen, benzyl, benzyloxy or benzylthio or substituted derivatives thereof; R is hydrogen, halogen, hydroxy, alkyl or alkoxy, $A^1$ and $A^2$ are hydrogen or alkyl and Z is amine or azacyclohydrocarbonyloxy.

JP 49116035 discloses a process for making compounds of the formula

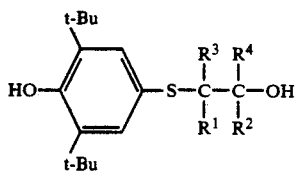

wherein $R^1$, $R^2$, $R^3$ and $R^4$ are hydrogen, alkyl or aryl groups, and $R^1$ and $R^2$ can be combined to form a cycloalkyl group. The compounds are said to be useful as drug intermediates, agricultural chemicals, antioxidants and industrial chemicals. Specifically disclosed is a compound of the formula

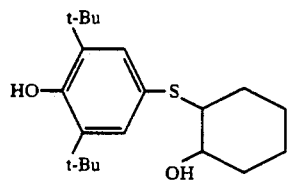

SUMMARY OF THE INVENTION

It is, therefore, a primary object of the present invention to provide novel cyclic phenolic thioethers pharmaceutical compositions containing them and methods of using them, as well as intermediates for producing them.

It is a further object of the present invention to provide methods for stimulating or inhibiting superoxide generation and to provide methods for treating conditions mediated by products of the arachidonic acid metabolic pathway and for promoting anti-inflammatory and/or anti-allergic effects in mammals in need thereof by the administration of preselected dosages of compounds of the present invention or pharmaceutically acceptable salts thereof in appropriate non-toxic pharmaceutical dosage forms or compositions.

Another object of the present invention is to provide dosage unit forms adapted for, e.g., oral, topical, and/or parenteral administration and useful in the stimulation or inhibition of superoxide generation and in the treatment, management and mitigation of inflammation, allergies, psoriasis and hypersensitivity reactions and related disorders and conditions in which physiologically active agents formed in the arachidonic acid metabolic pathway are involved.

Those compounds of the present invention which inhibit superoxide generation may be useful in the therapeutic or prophylactic treatment of disease conditions which are mediated wholly or partly by superoxide generation such as adult respiratory distress syndrome, superoxide mediated inflammatory or allergic conditions, and other medical conditions which are caused by or aggravated by superoxide.

Those compounds of Formula I which are stimulators of superoxide generation in neutrophils may be useful in the therapeutic or prophylactic treatment of disease conditions in which superoxide generation is an important factor.

Although it has been speculated that 5-lipoxygenase may be involved in superoxide generation, the ability of some compounds, which inhibit 5-lipoxygenase, to stimulate superoxide generation in neutrophils while others inhibit superoxide generation indicates that superoxide generation is not governed by 5-lipoxygenase. Thus the activity of the compounds of Formula I in stimulating or inhibiting superoxide generation is not related to the ability to inhibit 5-lipoxygenase. Compounds which do not inhibit 5-lipoxygenase may still act as inhibitors or stimulators of superoxide generation. In general those compounds of Formula I which are carboxylic acids inhibit superoxide generation and those compounds which are esters or heterocycle alkyl amides stimulate superoxide generation. Compounds of Formula I which are readily hydrolyzable to the carboxylic acid upon oral administration may also act as prodrugs which would be converted to superoxide inhibitors by stomach acid, blood, liver, or other organs.

In general, those compounds of Formula I wherein $R^1$ and $R^2$ are tert-alkyl or phenyl and A is sulfur are inhibitors of 5-lipoxygenase.

The present invention provides a method by which neutrophil activation and the generation of superoxide anions are accomplished utilizing compounds of Formula I having the ability to stimulate superoxide generation. Accordingly these compounds of Formula I are useful in the design and testing of anti-inflammatory properties of other pharmacologically active agents.

The ability to produce superoxide which may itself be microbicidal or which is then converted to toxic oxidants such as $H_2O_2$, OH, and singlet oxygen is important to the phagocytic killing mechanisms which enable neutrophils and macrophages to kill bacteria and parasites through phagocytosis.

Therefore, compounds of Formula I which stimulate superoxide generation may be useful in the adjunctive therapy of microbial infections. The compounds may also be useful in treating conditions such as Chediak-Higashi Syndrome in which the patient's macrophages and polymorphs are only weakly active causing the patients to suffer from recurring infections involving organisms with normally low pathogenicity. Compounds of Formula I may also be useful in the adjunctive therapy of patients whose immune systems have been weakened or impaired by disease or by chemotherapy or radiation therapy and who are more subject to microbial infections.

DETAILED DESCRIPTION OF THE PREFERRED EMBODIMENTS

These and other similar objects, advantages and features are accomplished according to the products, compositions and methods of the invention comprising compounds of the formula

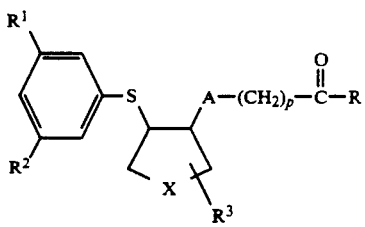 (I)

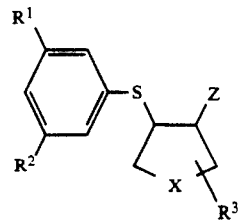 (III)

wherein $R^1$, $R^2$, $R^3$ and X, are defined as in Formula I, and Z represents hydroxy, halogen, sulfate ester, or perfluoroacyl ester.

The compounds of Formula III are useful as intermediates for making compounds of Formula I.

More preferred compounds of the present invention are compounds of the formula IV:

and the pharmaceutically acceptable salts thereof wherein $R^1$ and $R^2$ are the same or different and independently represent tert-alkyl of 4 to 10 carbon atoms, phenyl, or hydrogen; $R^3$ represents hydrogen or alkyl of 1 to 4 carbon atoms; X represents O, S or $(CH_2)_m$ wherein m is 1 or 2; A represents O or $S(O)_n$ wherein n is 0, 1, or 2; p is an integer from 0 to 4; and R represents:

(a) alkyl of 1 to 4 carbon atoms;
(b) OH;
(c) $OR^4$ wherein $R^4$ is alkyl of 1 to 4 carbon atoms;
(d) $NR^5R^6$ wherein $R^5$ is hydrogen or alkyl, and $R^6$ is hydrogen, alkyl, heterocyclealkyl, substituted heterocyclealkyl, cycloalkyl, substituted cycloalkyl, phenyl, substituted phenyl, phenylalkyl, or substituted phenylalkyl, or $NR^5R^6$ together form a heterocyclic ring which may optionally be substituted; or
(e) $(CH_2)_tCOOR^7$ wherein t is an integer from 1 to 4 and $R^7$ is hydrogen or alkyl of 1 to 4 carbon atoms.

Included in the present invention are compounds of the formula

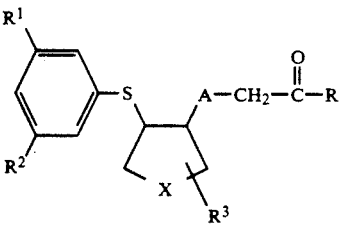 (II)

and the pharmaceutically acceptable salts thereof wherein $R^1$ and $R^2$ are the same or different and independently represent tert-butyl, phenyl, or hydrogen with the proviso that when $R^1$ is hydrogen, $R^2$ is tert-butyl or phenyl; $R^3$ represents hydrogen or alkyl of 1 to 4 carbon atoms; X represents $(CH_2)_m$ wherein m is 1 or 2; A represents O or S; and R represents:

(a) OH;
(b) $OR^4$ wherein $R^4$ is alkyl of 1 to 4 carbon atoms; or
(c) $NR^5R^6$ wherein $R^5$ is hydrogen or alkyl of 1 to 4 carbon atoms and $R^6$ is hydrogen, alkyl of 1 to 4 carbon atoms or heterocyclealkyl wherein the alkyl moiety has 1 to 4 carbon atoms; or $NR^5R^6$ together form a heterocyclic ring which may optionally be substituted.

Also included in the present invention are novel intermediates of the Formula III

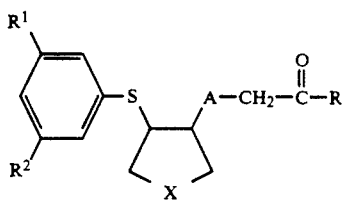 (IV)

wherein $R^1$ and $R^2$ are the same or different and independently represent tert-butyl, phenyl or hydrogen with the proviso that when $R^1$ is hydrogen, $R^2$ is tert-butyl or phenyl; X is $(CH_2)_m$ wherein m is 2, A is S or O; and R is:

(a) OH;
(b) $OR^4$ wherein $R^4$ is alkyl of 1 to 4 carbon atoms; or
(c) $NR^5R^6$ wherein $R^5$ is alkyl of 1 to 4 carbon atoms and $R^6$ is alkyl of 1 to 4 carbon atoms or heterocyclealkyl wherein the alkyl moiety has 1 to 4 carbon atoms and the pharmaceutically acceptable salts thereof.

Particularly preferred compounds of formula I are those wherein $R^1$ and $R^2$ are both tert-butyl; X is $(CH_2)_m$ wherein m is 2; A is S or O; and R is:

(a) OH;
(b) $OR^4$ wherein $R^4$ is alkyl of 1 to 2 carbon atoms; or
(c) $NR^5R^6$ wherein $R^5$ alkyl of 1 to 4 carbon atoms and $R^6$ is heterocyclealkyl wherein the alkyl moiety has 1 to 4 carbon atoms;

and the pharmaceutically acceptable salts thereof.

Compounds of Formula I can possess one or more asymmetric atoms and are thus capable of existing in the form of optical isomers as well as in the form of racemic or nonracemic mixtures thereof. The optical isomers can be obtained by resolution of the racemic mixtures by conventional processes. Included in the family of compounds of Formula I and Formula III are all isomeric forms thereof, including diastereoisomers, geometric isomers, and the pharmaceutically acceptable salts thereof.

The term "tert-alkyl" as used herein in reference to $R^1$ and $R^2$ refers to branched chain alkyl moieties of from about 4 to about 10 carbon atoms having a tertiary carbon atom attached to the phenyl ring substituted by $R^1$ and $R^2$. Examples of such groups are tert-butyl, i.e., 1,1-dimethylethyl, 1-1-dimethylpropyl, 1-methyl-1-(ethyl)pentyl, 1,1-diethylpropyl, 1-ethyl-1-(propyl)butyl and the like.

The term "alkyl" defines straight or branched chain monovalent hydrocarbon radicals having between about 1 to 6 carbon atoms including, for example, methyl, ethyl, propyl, isopropyl, butyl, t-butyl, pentyl, 1-methylbutyl, isopentyl, neopentyl, hexyl, etc.

The terms "heterocycle" and "heterocyclic ring" as used herein refer to aromatic or nonaromatic heterocyclic rings which contain one or more heteroatoms and include but are not limited to pyridine, piperazine, piperidine, morpholine, azabicycloalkyl, e.g., 3-azabicyclo[3,2,2]nonane, azatricycloalkyl, 1,2,3,4-tetrahydroisoquinoline, 5,6,11,12-tetrahydrodibenz[b,f]azocine, iminostilbene, and the like which may optionally be substituted with one or more substituents selected from alkyl, phenyl, substituted phenyl, phenylalkyl, heterocycle, cycloalkyl, halogen, hydroxy and lower alkoxy.

The terms "substituted phenyl" and "substituted phenylalkyl" as used herein refer to phenyl or phenylalkyl moieties in which the phenyl ring is substituted by one or more substituents selected from alkyl, hydroxy, alkoxy, halogen, alkylamino, dialkylamino, phenyl and alkyl carbonyl.

The term "cycloalkyl" refers to cycloalkyl rings of 3 to 10 carbon atoms and includes but is not limited to cyclopentyl, cyclohexyl, adamantane, norbornane and the like which may optionally be substituted by 1 or more substituents selected from alkyl, hydroxy, alkoxy, and halogen.

The term "halogen" refers to chlorine, bromine, fluorine, and iodine.

The expression "pharmaceutically acceptable salts" is intended to include those salts capable of being formed with the compounds of the present invention, e.g., when R represents OH, $NR^5R^6$ or alkyl carboxyl, without materially altering the chemical structure or pharmacological properties thereof. Such salt include inorganic and organic cations or acid addition salts, such as sodium, potassium, calcium, ammonium, alkylammonium, quaternary ammonium, triethanolamine, lysine, hydrochloric, hydrobromide, etc. well known to those skilled in the art. The foregoing salts are prepared in the conventional manner by neutralization of the compounds of formula I with the desired base or acid.

The compounds of the present invention can be administered to a patient in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between 0.1 mg/kg/day to about 100 mg/kg/day and preferably between about 0.5 mg/kg/day to about 50 mg/kg/day when administered to patients suffering from inflammation or allergic or hypersensitivity reactions. The compounds may also be administered transdermally or topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of the invention are prepared from readily available starting materials by any of the following alternate processes in a conventional manner. The following reaction schemes describe methods which can be employed for preparing the compounds of formula I, including starting materials, intermediates, and reaction conditions.

As shown in part (1) of Scheme A, a mercaptan (V) can be reacted with an oxabicyclo compound (VI) to give the intermediate (III) which may then be reacted with a monohaloacid in a base or alternatively with a thiol acid in an acid to obtain a product acid of type (VII). Epoxides of type (VI) are readily prepared by oxidation of a double bond with peroxides such as m-chloroperbenzoic acid, peracetic acid, per trifluoroacetic acids, hydrogen peroxide, t-butyl hydroperoxide and the like. Base induced cyclization of halohydrins, obtained by treatment of double bonds with mineral acids, also produces epoxides. In addition, epoxides can be used as starting materials for the preparation of halohydrins which can also be used to produce compounds of type III, following reaction with, for example, a mercaptan. Most bases can be used for the preparation of III, for example, hydroxides, tert-amines, heterocyclic amines, dimethylaminopyridines, hydrides, lithium alkyls, lithium amides and the like, since the thiolate anion is an exceptional nucleophile. Non-nucleophilic bases are preferred for the conversion of III into VII in the presence of an electrophilic reagent such as a substituted halo alkyl group.

Compound III may also be converted into VII via conversion into a halo compound (Scheme C), an activated ester (Scheme C) or acid catalysis (Scheme A). In the first case, treatment of the hydroxy compound with hydrochloric, hydrobromic, hydriodic or hydrofluoric acid, preferably at reflux temperatures, converts it into the corresponding halo compound. Displacement of the halogen (SN₂) with a mercaptan under basic conditions (as shown in Scheme B) provides compound XIII.

The alcohols III or XI may be converted into activated esters such as those of toluene sulfonic acid (tosylates), methane sulfonic acid (mesylates), trifluoromethane sulfonic acid Triflates) and trifluoroacetic acid. Displacement of the activated ester (SN₂) with a mercaptan under basic conditions (see above) provides compound VII. Both this method and that outlined above utilizing a halo intermediate have the advantage that the stereochemistry at the carbon bearing the functional group may be inverted thus allowing control (selection) of the stereochemistry (cis or trans) of the product.

Treatment of alcohols III or XI with a mercaptan in the presence of an acid (Scheme A, B, C) should provide the corresponding sulfide, e.g., VII or XIII. Mineral acids, organic acids and Lewis acids are suitable for this reaction. Non-nucleophilic acids are preferred and include, for example, trifluoroacetic acid, toluene sulfonic acid, perfluorobutyric acid, triflic acid, phosphoric acid, sulfuric acid, boron trifloride, aluminum chloride and the like.

Conversion of a carboxylic acid such as VII, XI or XII into an ester or an amide is accomplished by standard means. The carboxylic acid may be treated with the appropriate alcohol with or without added solvent in the presence of an acid (see above) to provide the product ester. A salt of the carboxylic acid may be prepared by treatment with a base (see above) and the salt then treated with an electrophilic group with displacement of, for example, a halide, tosylate and the like. An alternative method of preparation is conversion of the carboxylic acid into an activate carbonyl function such as an acid halide, mixed anhydride or activated ester followed by treatment with an appropriate alcohol or amine. Acid halides can be made by mixing, for example, thionyl chloride, thionyl bromide, phosphorus trichloride, phosphorus pentabromide, oxalyl chloride and the like with the acid. Mixed anhydrides with, e.g., isobutyl chloroformate, are prepared in the standard manner with the acid being treated with isobutyl chloroformate in the presence of a base or from a preformed carboxylate salt. The same type of salt, either prepared in the reaction or preformed, can be treated with for example, N-chlorosuccinimide, to form the succinimide activated ester. Treatment of either of these intermediates with the appropriate amine, alcohol, mercaptan or electrophile will provide the compounds of this invention.

The conversion of the alcohols/mercaptans III, XI, XVI, XVII and the like into compounds of, for example, X, is accomplished in the same manner as the synthesis of the other esters outlined above. In this case, the appropriate alcohol/mercaptan is represented as outlined above and the acylating agent is an acid halide or anhydride.

Scheme C illustrates yet another method for the preparation of the intermediates and compounds of this invention. An alpha-halo ketone, substituted or unsubstituted, is treated with a oxygen or sulfur nucleophile generated as described above. The valuable intermediate, XV, is reduced directly with, for example, a hydride reducing agent such as sodium borohydride, lithium aluminum hydride, sodium cyano borohydride and the like or borane, to provide the alcohols III and XI. The use of these intermediates for the preparation of compounds VII, VIII, XIV and X is discussed above. Conversion of ketone XV into a thioketone is readily accomplished using reagents such as phosphorus pentasulfide or 2,4-bis(4-methoxyphenyl)-1,3-dithia-2,4-diphosphetane-2,4-disulfide (Lawesson's Reagent). Reduction of the thioketone as discussed above for the ketones provides the mercaptan analogs of III and XI and it is used similarly.

SCHEME A

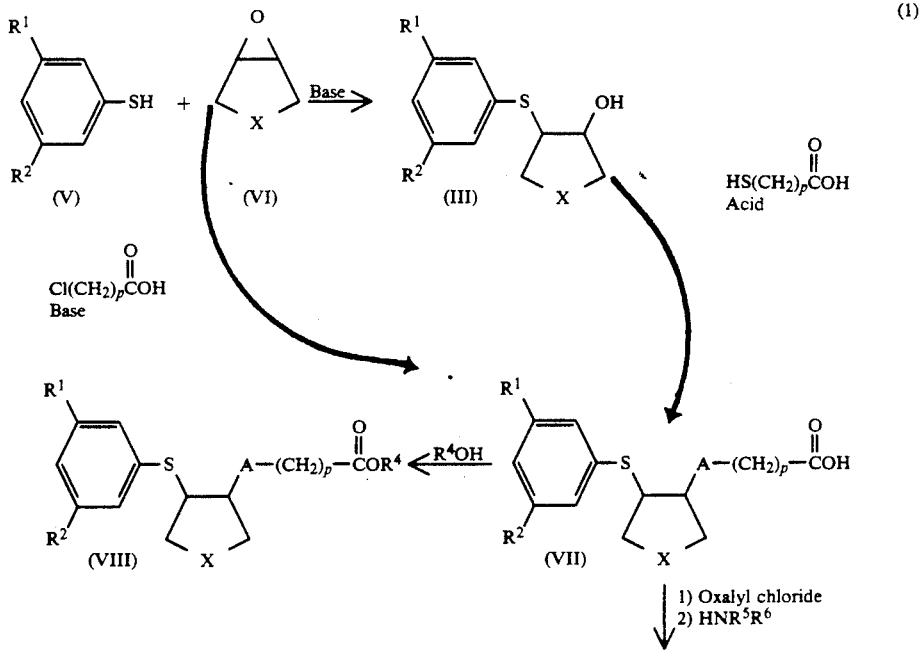

SCHEME A
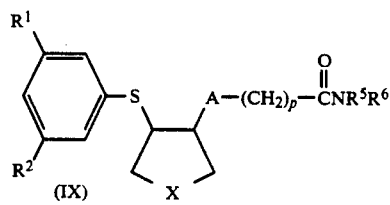
(IX)
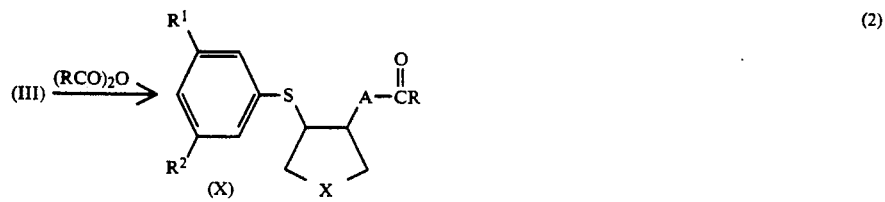
(2)
$R$ = alkyl or $(CH_2)_rCOOR^7$
SCHEME B
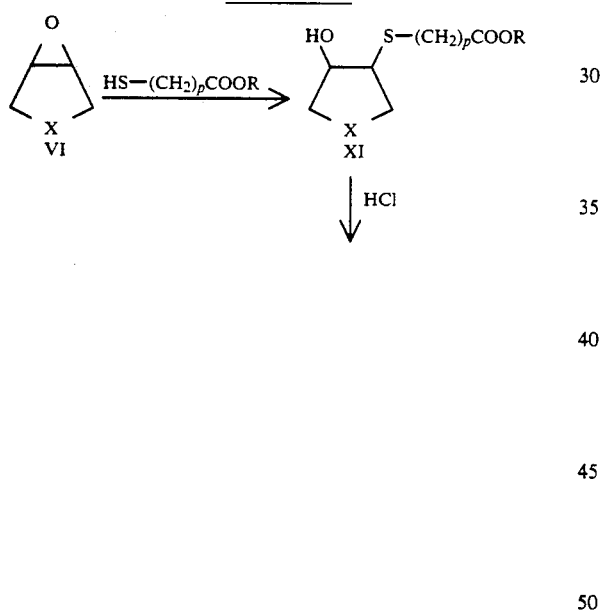
-continued SCHEME B
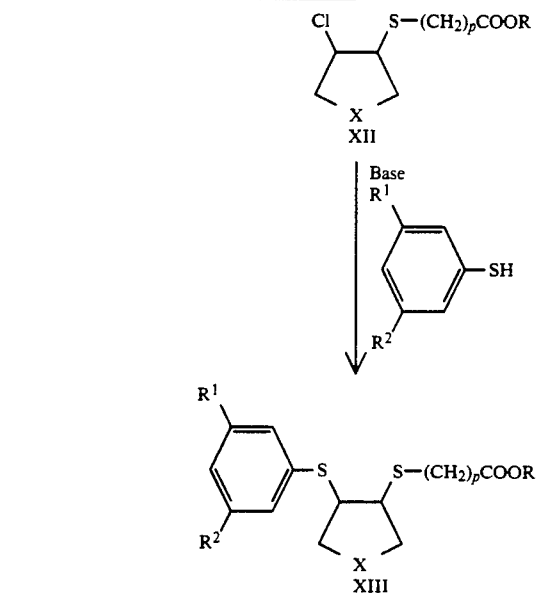
SCHEME C
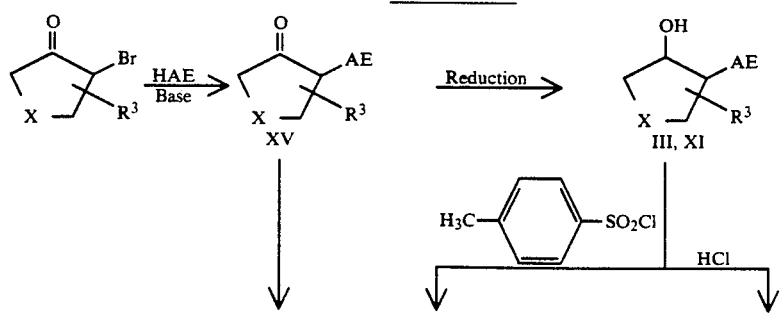

SCHEME C -continued

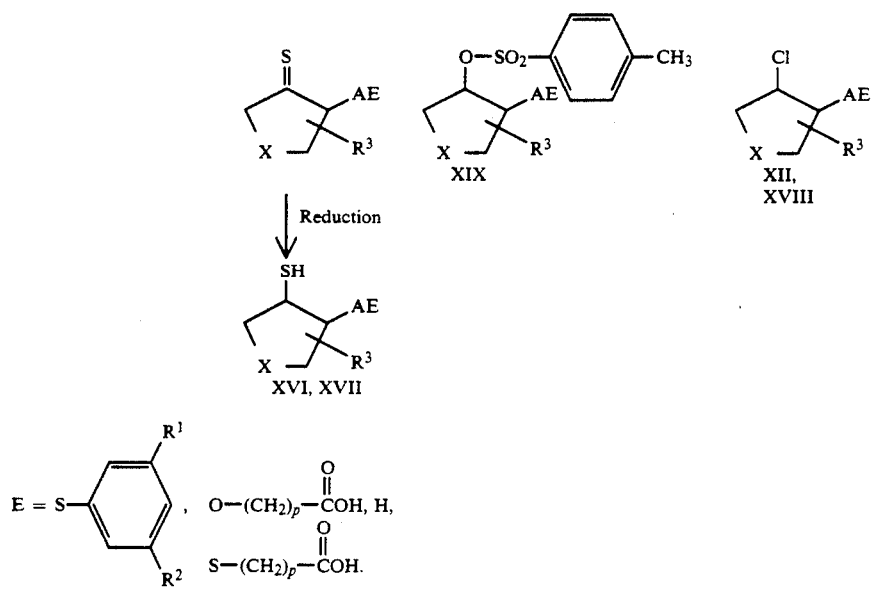

BIOLOGICAL EVALUATIONS

The compounds of the invention are evaluated with respect to superoxide modulating activity according to the following assay procedure:

Human neutrophil superoxide generation: Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. *J. Biol. Chem.* 256: 12640–12643, 1981.) To 5 million neutrophils in 2.85 ml of Krebs-Ringer phosphate buffer, pH 7.2, 50 ul of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading minus the initial reading (before addition of FMLP) was used to calculate nanomoles of superoxide generated based on a molar extinction coefficient of $2.1 \times 10^4$ cm$^{-1}$mole$^{-1}$.

Isolation of human neutrophils: Human neutrophils were isolated from freshly drawn blood of healthy donors. Two ml of 5% dextran (MW 200,000-300,000) in saline was added to 10 ml aliquots of blood, mixed and placed upright for 45 min. at 37° C. Approx. 8-10 ml of the plasma-white cell suspension from the dextran sedimentation was layered on 3 ml of Ficol-paque in a 15 ml tube and centrifuged at 400 g for 30 min. The supernate, containing plasma and platelets, was discarded by aspiration, and the pellet, containing predominantly neutrophils, was resuspended in 1 ml saline. The suspension was transferred to a clean tube, and pooled with other aliquots of blood treated similarly. The pooled suspension was centrifuged at 350 g for 5 min. and supernate discarded. The pellet was resuspended in 5 ml of 0.05% NaCl with a plastic Pasteur pipette for 25 seconds to lyse contaminating red cells, then 5 ml of 1.75% NaCl added to regain isotonicity. The red cell lysing procedure was repeated, the cells suspended in appropriate buffer (depending on assay) and counted.

The compounds of the present invention evaluated with respect to cyclooxygenase inhibition according to the following assay procedure.

Inhibition of Sheep Seminal Vesicle Microsome Cyclooxygenase

The assay was based on oxygen consumption during conversion of arachidonic acid to prostaglandin $G_2$ catalyzed by cyclooxygenase *Biochem.* 11:3276–3285 (1972). Lyophilized ovine microsome (approx. 1 mg) suspended in 2.9 ml Tris-HCl buffer, pH 8.2, containing 0.7 mM phenol were used as source of arachidonate cyclooxygenase. The inhibitor, 50 μl in DMSO, was added and the mixture preincubated for 5 minutes at 37° C. Fifty μl of arachidonic acid (final conc. 50 μM) was added to start the reaction. The slopes of the initial rates of oxygen uptake, in the presence and absence of inhibitor, were compared to determine reaction inhibition. Percent inhibition was computed using the following formula:

$$\% \text{ Inhib.} = \frac{I.S.^* \text{ (control)} - I.S. \text{ (inhib.)}}{I.S. \text{ (Control)}} \times 100$$

*I.S. = initial slope.

The compounds of the invention are evaluated with respect to 5-lipoxygenase inhibition according to the following assay procedure.

Inhibition of 5-lipoxygenase, in vitro: anti-inflammatory, anti-allergy activities.

The 100,000 x g supernatant fraction of Rat Basophilic Leukemia Cell Homogenate (RBL-1) serves as a 5-lipoxygenase enzyme source. The enzyme is incubated with [1-$^{14}$C]-arachidonic acid and Ca++ in the presence and absence of test compound. The product of 5-lipoxygenase, 5-hydroxyeicosatetraenoic acid (5-HETE), is separated by thin-layer chromatography an measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

For comparison the compound of Formula XX, a known 5-lipoxygenase inhibitor described in U.S. Pat. No. 4,755,524 was used.

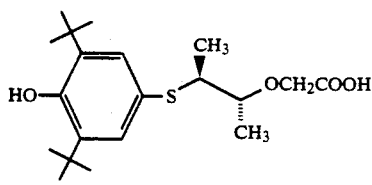

(XX)

(±)[2S*-[[3,5-bis(1,1-dimethylethyl)-4-hydroxyphenyl]thio]-1R*-methylpropoxy]acetic acid The results with respect to certain compounds of the present invention are set forth in Table I below.

TABLE 1

| Compound Example Number | 5-Lipoxygenase Inhibition IC$_{50}$ (μM) | FMLP Induced Superoxide Generation | Cyclooxygenase Inhibition IC$_{50}$ (μM) |
|---|---|---|---|
| 4 | — | Stimulation 1 μM, 67% > control 10 μM, 133% > control 100 μM, 167% > control | — |
| 5 | 100 | Inhibition IC$_{50}$ = 1.1 μM | — |
| 7 | Stimulated 45% at $10^{-4}$M Stimulated 27% at $10^{-5}$M | Inhibition IC$_{50}$ = 50 μM | Inactive at 100 μM |
| 11 | Stimulated 2.5% at $10^{-4}$M Stimulated 3.2% $10^{-5}$M | Inhibition IC$_{50}$ = 4.8 μM | 2.9 |
| 15 | Inhibited 21.3% at $10^{-4}$M Inhibited 14.9% at $10^{-5}$M | Inhibition IC$_{50}$ = 2.8 μM | 64.0 |
| 16 | 100 | Stimulation 10 μM, 33% > control 25 μM, 83% > control 50 μM 100% > control | — |
| 17 | >100 | Inhibition IC$_{50}$ = 3.4 μM | — |
| Formula XX | 4.9 | Inhibition IC$_{50}$ = 11 μM | — |

The compound of Formula XX inhibited both superoxide generation and 5-lipoxygenase whereas the compound of Example 16 inhibited 5-lipoxygenase and stimulated superoxide generation. This data indicates that superoxide generation is not dependent on 5-lipoxygenase and that the ability of a compound to inhibit 5-lipoxygenase is not related to its ability to simulate superoxide generation.

The compound of Example 7, which has no substituents on the phenyl ring (i.e., $R^1$ and $R^2$=H) did not inhibit either 5-lipoxygenase or cyclooxygenase but did inhibit superoxide generation.

Complement C5a induced superoxide generation may also be stimulated or inhibited by compounds of the present invention.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed. And such expected variations or differences in results are contemplated in accordance with the objects and practices of the present invention. It is intended, therefore, that the invention be limited only by the scope of the claims which follow.

The following non-limiting examples further illustrate details for the preparation of the compounds of the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus and are uncorrected.

EXAMPLE 1

O-[3,5-bis(1,1-dimethylethyl)phenyl] dimethylcarbamothioate

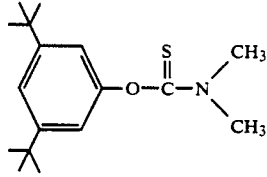

Potassium hexylmethyl disilane (15% by weight in toluene, 260 ml, 0.169 moles) was added by syringe to a solution of 3,5-di-tert-butylphenol (34.8 g, 0.169 moles) in tetrahydrofuran (500 ml). After 30 minutes, a solution of dimethylthiocarbamoyl chloride (24.7 g, 0.20 moles) in tetrahydrofuran (50 ml) was added over 10 minutes. The reaction mixture was stirred at room temperature for 30 minutes then at 50° C. for 1.5 hours. After cooling to room temperature, the reaction mixture was poured into cold (0° C.) water (100 ml) containing potassium hydroxide (30 g). The mixture was extracted twice with 1000 ml of ethyl ether. The combined ethyl ether extracts were dried over sodium sulfate, filtered and concentrated with a rotary evaporator to give the crude product as a yellow oil. The title product was purified by chromatography on silica gel and used directly in the next Example 2.

EXAMPLE 2

3,5-bis(1,1-dimethylethyl)benzenethiol

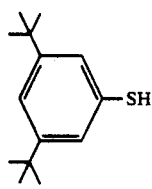

The compound of Example 1 (42 g, 0.143 moles) was heated to 300° C. in a round bottom flask with a heating mantle for 2 hours. After cooling to room temperature the material was dissolved in ethylene glycol (100 ml). A solution of potassium hydroxide (12.0 g, 0.214 moles) in water (20 ml) was added and the reaction mixture was heated to 123° C. for 3.5 hrs. After stirring at room temperature for 20 hours, the reaction mixture was cooled to 0° C. with an ice bath, and 10% hydrochloric acid was added slowly to adjust the pH to 2.0. The reaction mixture was extracted twice with 100 ml of ethyl acetate. The combined ethyl acetate extracts were washed with brine (100 ml), dried over sodium sulfate, filtered and concentrated to an oil. The title product was purified by silica gel chromatography and recrystallized from pentane, m.p. ca. 58° C. The structure assignment was supported by NMR, infrared spectroscopy and elemental analysis.

Analysis calculated for: $C_{14}H_{22}S$ (m.w.=22.4):

Theory: C, 75.61; H, 9.71; S, 14.42. Found: C, 75.55; H, 10.07; S, 14.34.

EXAMPLE 3 trans-2-[[3,5-bis(1,1-dimethylethyl) phenyl]thio]cyclohexanol

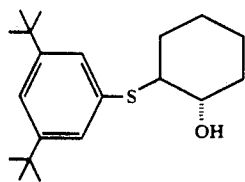

3,5-Bis(1,1-dimethylethyl)benzenethiol (Example 2) (5.0 g, 0.0225 moles) was added to freshly prepared sodium ethoxide (0.0230 moles) in absolute ethyl alcohol (50 ml). After stirring for 1 hour, cyclohexene oxide (2.2 g; 0.0225 moles) was added by syringe over 5 minutes, and the reaction mixture was stirred for 60 hours at room temperature. Water (100 ml) was added, and the reaction mixture was extracted twice with 75 ml of ethyl acetate. The combined ethyl acetate extracts were washed with brine (50 ml) dried over sodium sulfate, filtered and concentrated to give the product as a yellow solid which was recrystallized from cold pentane. The structure assignment was supported by NMR spectroscopy. The title compound was used in Example 4.

EXAMPLE 4

Methyl trans-[[2-[[3,5-bis(1,1-dimethylethyl) phenyl]thio]cyclohexyl]thio]acetate

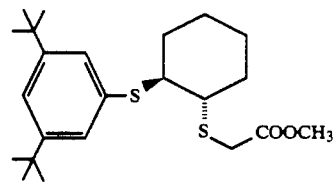

Methyl thioglycolate (2.65 g, 0.025 moles) was added by syringe to a solution of trans-2-[[3,5-bis(1,1-dimethylethyl)phenyl]thio]cyclohexanol (5.0 g., 0.025 moles) in methylene chloride (10 ml). After stirring the reaction mixture for 15 minutes, trifluoroacetic acid (10 ml) was added by syringe, and the reaction mixture was stirred for 20 hours at room temperature. The reaction mixture was poured into cold water (100 ml). After stirring for 30 minutes, the mixture was extracted with ethyl acetate. The aqueous layer was washed with ethyl acetate (50 ml). The combined ethyl acetate extracts were washed twice with 75 ml of water, dried over sodium sulfate, filtered and concentrated to give the crude product as an oil. The title compound was purified by silica gel chromatography and dried in a vacuum oven at 60° C. for 3 hours. The structure assignment was supported by NMR, infrared spectroscopy, and elemental analysis.

Analysis calculated for: $C_{23}H_{36}O_2S_2$ (m.w.=408.66):

Theory: C, 67.60; H, 8.88; S, 15.69. Found: C, 67.62; H, 9.13; S, 15.58.

EXAMPLE 5 trans-[[2-[[3,5-bis(1,1-dimethylethyl)phenyl] thio]cyclohexyl]thio]acetate acid

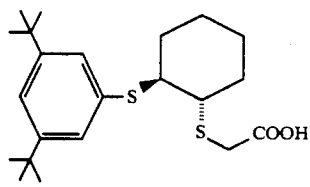

Water was added to a solution of the compound of Example 4 (9.2 g, 0.0255 moles) in methyl alcohol (100 ml) until the solution became cloudy. Lithium hydroxide hydrate (1.75 g, 0.0675 moles) was added, and the reaction mixture was stirred at room temperature. Periodically, water was added to make the solution cloudy. After 6 hours, the solution was made acidic with 10% hydrochloric acid and extracted with ethyl acetate. The ethyl acetate extract was dried over sodium sulfate, filtered, and concentrated to give the crude product as an oil. The product was purified by silica gel chromatography. The structure assignment was supported by NMR and elemental analysis.

Analysis calculated for: $C_{22}H_{34}S_2O_2$ (m.w.=394.63):

Theory: C, 66.96; H, 8.68; S, 16.25. Found: C, 66.92; H, 8.80; S, 16.00.

EXAMPLE 6 trans-2-(phenylthio)cyclohexanol

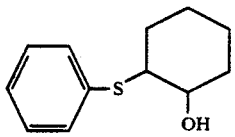

Thiophenol (2.14 g, 0.0194 mole) was added to freshly prepared sodium ethoxide (sodium, 0.45 g) in ethanol (30 ml). After several minutes, cyclohexene oxide was added, and the reaction mixture was stirred at room temperature for 24 hours. The reaction mixture was concentrated with a gentle flow of nitrogen gas. The residue was dissolved in diethyl ether (75 ml) and washed with 1N hydrochloric acid (19 ml). The diethyl ether was washed three times with 50 ml of 5% sodium carbonate, once with 0.5N hydrochloric acid (50 ml) and once with brine (25 ml), dried over anhydrous magnesium sulphate, filtered and concentrated with a rotary evaporator to give the product as an oil. The structure was supported by NMR and infrared spectroscopy.

EXAMPLE 7

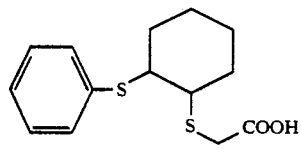

Mercaptoacetic acid (0.44 g, 0.0048 mole) was added to a cold solution of the compound of Example 6 (1.0 g 0.0048 mole) in methylene chloride (5 ml) containing trifluoracetic acid (3.5 ml). The reaction mixture was stirred at room temperature for 20 hours. The reaction mixture was concentrated to an oil with a rotary evaporator. The residue was dissolved in diethyl ether (50 ml), washed three times with 20 ml of 5% sodium bicarbonate, followed by 1N hydrochloric acid (10 ml) and water (20 ml), dried over anhydrous magnesium sulfate, filtered and concentrated to a colorless oil with a rotary evaporator. The product was purified by silica gel chromatography. The structure was supported by NMR, infrared spectroscopy and elemental analysis.

Analysis calculated for: $C_{14}H_{18}S_2O_7$ (m.w.=282.44):
Theory: C, 59.54; H, 6.42; S, 22.70. Found: C, 59.36; H, 6.57; S, 22.43.

EXAMPLE 8

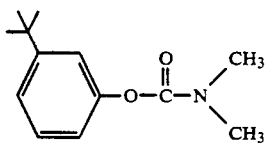

meta-t-Butyl phenol (30.0 g, 0.20 mole) was added to water (140 ml) containing potassium hydroxide (11.2 g, 0.20 mole) and stored at 0° C. for 20 hours. Dimethyl thiocarbamoyl chloride (32.8 g, 0.265 mole) was added as a solution in tetrahydrofuran (60 ml) to the cold solution with stirring. The ice bath was removed, and the turbid solution was stirred for 15 minutes. To this mixture was added 10% potassium hydroxide (75 ml). The reaction mixture was extracted three times with 125 ml of benzene. The combined benzene extracts were washed with brine (75 ml) and concentrated in a rotary evaporator to give the crude product as an oil. The product was purified by silica gel chromatography. The structure was supported by NMR.

EXAMPLE 9

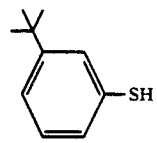

Starting with O-[3-(1,1-dimethylethyl)phenyl]dimethylcarbamothioate and following the procedure described in Example 2, the title compound was obtained.

EXAMPLE 10

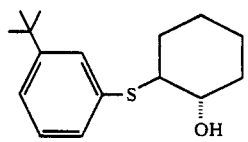

Using the method of Example 6 and substituting 3-(1,1-dimethylethyl)benzenethiol for thiophenol, the title compound was obtained.

EXAMPLE 11

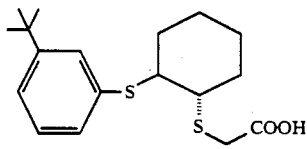

Trifluoracetic acid (10 ml) was added to a solution of the compound of Example 10 (3.6 g, 0.0136 mole) in methylene chloride (5 ml) with stirring. After several minutes, methyl thioglycolate (1.59 g, 0.015 mole) was added, and the reaction mixture was stirred for 30 minutes. The reaction mixture was poured into methanol (50 ml) containing lithium hydroxide hydrate (12.6 g, 0.30 mole). Water (125 ml) was slowly added to the mixture and then the mixture was extracted with diethyl ether (100 ml). The aqueous phase was acidified with concentrated hydrochloric acid and extracted twice with 100 ml of diethyl ether. The combined diethyl ether extracts were washed with water (30 ml), 5% sodium bicarbonate (50 ml) and brine (50 ml), dried over anhydrous magnesium sulfate, filtered and concentrated with a rotary evaporator to give the crude product as an oil. The product was purified by silica gel chromatography. The structure was supported by NMR, infrared spectroscopy, and elemental analysis.

Analysis calculated for: $C_{18}H_{26}S_2O_2$ (m.w.=338.52):
Theory: C, 63.87; H, 7.74; S, 18.94. Found: C, 64.00; H, 8.02; S, 19.10.

EXAMPLE 12

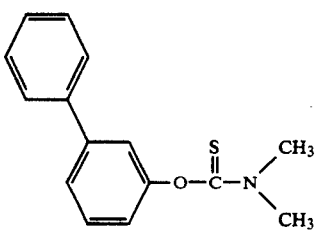

Using the method of Example 8 and substituting meta-phenyl phenol for meta-t-butyl phenol the title compound was prepared. The structure was supported by NMR.

EXAMPLE 13

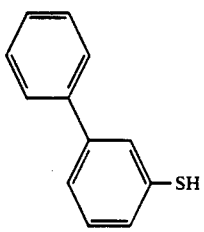

Starting with [1,1'-biphenyl]-3-yl dimethylcarbamoate and using the procedure described in Example 2, the title compound was obtained.

EXAMPLE 14

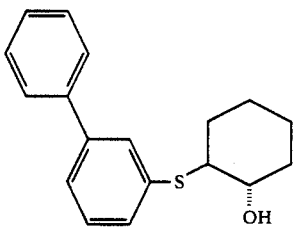

Starting with 3-[1,1'-biphenyl]thiol and following the procedure described in Example 3 gave the title compound.

EXAMPLE 15

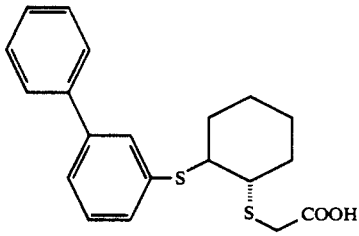

Starting with trans-2-[([1,1'-biphenyl]-3-yl)thio]cyclohexanol and using the method described in Example 11 gave the title compound. The structure was supported by NMR, infrared spectroscopy and elemental analysis.

Analysis calculated for: $C_{20}H_{22}S_2O_2$ (m.w.=358.51):

Theory: C, 67.00; H, 6.18; S, 17.89. Found: C, 66.94; H, 6.30; S, 18.07.

EXAMPLE 16

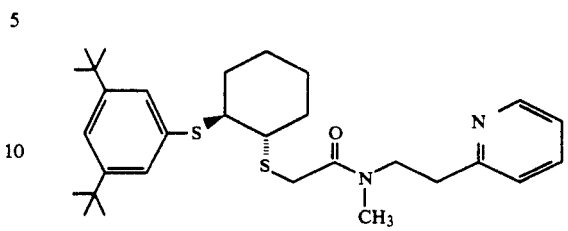

Oxalyl chloride (0.19 g, 0.0015 moles) was added by syringe to a cold (10° C.) solution of trans-[[2-[[3,5-bis(1,1-dimethylethyl)phenyl]thio]cyclohexyl]thio]acetic acid (Example 5) (0.55 g, 0.0014 moles) in benzene (50 ml). The cold bath was removed and the reaction mixture was stirred at room temperature for 20 hours. The reaction mixture was concentrated to an oil using a rotary evaporator. The oil was dissolved in toluene (50 ml) and concentrated to an oil. The process was repeated using tetrahydrofuran (25 ml) instead of toluene. The residue was dissolved in tetrahydrofuran (50 ml). To this solution was added 2-(2-methylaminoethyl)pyridine (0.19 g, 0.0014 moles) and triethylamine (0.22 g) and the reaction mixture was stirred at room temperature for 48 hours. The white solid precipitate was removed by filtration and washed with ethyl acetate (25 ml). The filtrate was concentrated to give the crude product as an oil. The produce was purified by silica gel chromatography and dried in vacuo at 100° C. for 1 hour to give the title compound. The structure assignment was supported by NMR, infrared spectroscopy and elemental analysis.

Analysis calculated for: $C_{30}H_{44}N_2O_2S_2$ (m.w.=512.83):

Theory: C, 70.26; H, 8.65; S, 5.45. Found: C, 69.96; H, 8.76; S, 5.43.

EXAMPLE 17

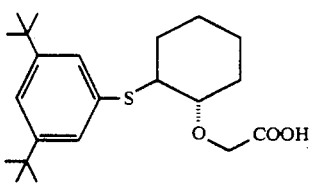

Sodium hydride (0.33 g, 0.0138 mole) was added to a solution of trans-2-[[3,5-bis(1,1-dimethylethyl)phenyl]thio]cyclohexanol (3.4 g, 0.0106 mole) in tetrahydrofuran (50 ml) at 0° C. After stirring the reaction mixture for 1.5 hr, the tetrahydrofuran was removed by rotary evaporation. Dimethyl sulfoxide (75 ml) was added followed by chloroacetic acid sodium salt (1.48 g, 0.0127 mole) and the reaction mixture was stirred at room temperature for 10 days. Water (100 ml) was added dropwise to the mixture followed by 10% hydrochloric acid (10 ml). The product was extracted twice with 200 ml of ethyl acetate. The combined ethyl acetate extracts were washed twice with 200 ml of water, dried over anhydrous sodium sulfate, filtered, and concentrated. The product was purified by chromatography on silica gel. The structure was supported by NMR and elemental analysis (378.6+¼ mole $H_2O$).

Analysis calculated for: $C_{22}H_{34}O_3S + \frac{1}{4}$ mole $H_2O$:
Theory: C, 68.98; H, 9.08; S, 8.37. Found: C, 69.12; H, 9.21; S, 8.27.

EXAMPLE 18

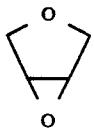

2,5-Dihydrofuran (DHF) (13.2 g, 0.188 mole) was added by syringe to a solution containing 3-chloroperoxybenzoic acid (29.1 g, 0.198 mole) and trifuloroacetic acid (0.5 ml) in methylene chloride (500 ml). After stirring at room temperature for 20 hours, the white solid was removed by filtration. The filtrate was washed with a solution of sodium carbonate (100 ml, saturated). The organic phase was stirred with solid sodium carbonate and sodium thiosulfate for 20 minutes and filtered. The product was purified by low pressure distillation (41° C./5 mmHg). The structure was supported by NMR.

EXAMPLE 19

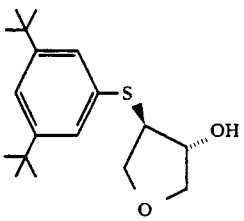

2,6-bis(1,1-Dimethylethyl)-4-benzenethiol (0.0078 mole) and the compound of Example 18 (0.0074 mole) are added to a degassed (Argon) solution of 50% sodium hydroxide (5 ml) and isopropyl alcohol (50 ml). The reaction is heated to reflux for 24 hours. The reaction is cooled to room temperature and poured into water (125 ml). The solution is made acidic with 1N hydrochloric acid and extracted 3 times with 100 ml of diethyl ether. The combined diethyl ether extracts are dried over anhydrous magnesium sulfate, filtered and concentrated with a rotary evaporator. The product is purified by silica gel chromatography.

EXAMPLE 20

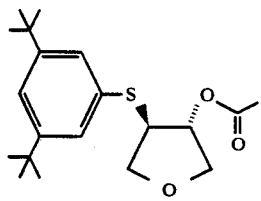

The compound of Example 19 (0.0062 mole) is added to acetic anhydride (20 ml). Triethylamine (0.0062 mole) is added, and the reaction mixture is stirred for 3 hours. Additional triethylamine (0.3 ml) is added, and the reaction mixture is stirred for 2 hours. The reaction mixture is concentrated to an oil with a gentle flow of nitrogen gas. The residue is dissolved in diethyl ether (75 ml), washed twice with 50 ml of 0.25N hydrochloric acid and once with 25 ml of brine, dried over anhydrous magnesium sulfate, filtered and concentrated with a gentle flow of nitrogen gas. The product is purified by silica gel chromatography.

EXAMPLE 21

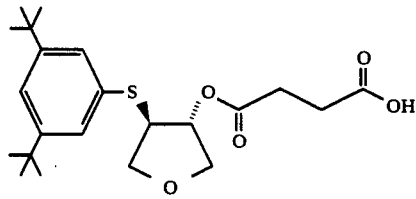

Succinic anhydride (0.0185 mole) and triethylamine (0.0185 mole) are added to a solution of tetrahydrofuran (THF) (50 ml) containing the compound of Example 19 (0.0092 mole). The reaction mixture is stirred for 3 days and then concentrated to an oil with a gentle flow of nitrogen gas. The residue is dissolved in diethyl ether. The solution is washed twice with 50 ml of water and once with 20 ml of 1N hydrochloric acid, dried over anhydrous magnesium sulfate, filtered and concentrated to an oil with a rotary evaporator. The product is purified by silica gel chromatography.

What is claimed is:

1. A compound of the formula:

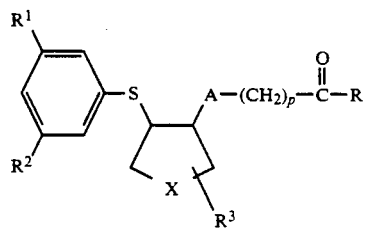

wherein $R^1$ and $R^2$ are the same or different and independently represent tert-alkyl of 4 to 10 carbon atoms, phenyl, or hydrogen with the exception that when R is alkyl, A is O, and p is O, $R^1$ and $R^2$ are not both hydrogen; $R^3$ represents hydrogen or alkyl of 1 to 4 carbon atoms; X represents $(CH_2)_m$ wherein m is 1 or 2; A represents O or $S(O)_n$ wherein n is 0, 1, or 2; p is an integer from 0 to 4; and R represents:

alkyl of 1 to 4 carbon atoms;
OH;
$OR^4$ wherein $R^4$ is alkyl of 1 to 4 carbon atoms;
$NR^5R^6$ wherein $R^5$ is hydrogen or alkyl, and $R^6$ is hydrogen, alkyl, cycloalkyl, substituted cycloalkyl having 1 or more substituents selected from the group consisting of alkyl, hydroxy, alkoxy, and halogen, phenyl, substituted phenyl having one or more substituents selected from the group consisting of alkyl, hydroxy, alkoxy, halogen, alkylamino, dialkylamino, phenyl and alkylcarbonyl, phenylalkyl, or substituted phenylalkyl wherein the phenyl ring has one or more substituents selected from the group consisting of alkyl, hydroxy, alkoxy, halogen, alkylamino, dialkylamino, phenyl and alkylcarbonyl; or
$(CH_2)_t COOR^7$ wherein t is an integer from 1 to 4 and $R^7$ is hydrogen or alkyl of 1 to 4 carbon atoms;

or a pharmaceutically acceptable salt thereof.

2. A compound according to claim 1 of the formula

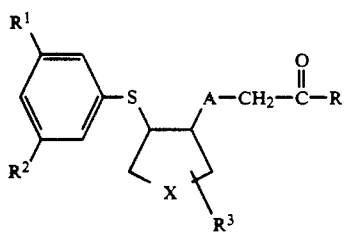

wherein $R^1$ and $R^2$ are the same or different and independently represent tert-butyl, phenyl, or hydrogen with the exception that $R^1$ and $R^2$ are not both hydrogen; $R^3$ represents hydrogen or alkyl of 1 to 4 carbon atoms; X represents $(CH_2)_m$ wherein m is 1 or 2; A represents O or S; and R represents:
OH;
$OR^4$ wherein $R^4$ is alkyl of 1 to 4 carbon atoms; or
$NR^5R^6$ wherein $R^5$ is hydrogen or alkyl of 1 to 4 carbon atoms and $R^6$ is hydrogen or alkyl of 1 to 4 carbon atoms;
or a pharmaceutically acceptable salt thereof.

3. A compound according to claim 2 of the formula

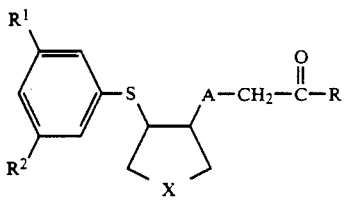

wherein $R^1$ and $R^2$ are the same or different and independently represent tert-butyl, phenyl, or hydrogen with the exception that $R^1$ and $R^2$ are not both hydrogen; X is $(CH_2)_m$ wherein m is 2, A is S or O; and R is:
OH;
$OR^4$ wherein $R^4$ is alkyl of 1 to 4 carbon atoms; or
$NR^5SR^6$ wherein $R^5$ is alkyl of 1 to 4 carbon atoms and $R^6$ is alkyl of 1 to 4 carbon atoms;
or a pharmaceutically acceptable salt thereof.

4. A compound according to claim 3 wherein $R^1$ and $R^2$ are tert-butyl; X is $(CH_2)_m$ wherein m is 2; A is S or O; and R is:
OH;
$OR^4$ wherein $R^4$ is alkyl of 1 to 4 carbon atoms; or
$NR^5R^6$ wherein $R^5$ is alkyl of 1 to 4 carbon atoms and $R^6$ is alkyl of 1 to 4 carbon atoms;
or a pharmaceutically acceptable salt thereof.

5. A compound according to claim 1 which is methyl trans-[[2-[[3,5-bis(1,1-dimethylethyl)phenyl]thio]cyclohexyl]thio]acetate.

6. A compound according to claim 1 which is trans-[[2-[[3,5-bis(1,1-dimethylethyl)phenyl]thio]cyclohexyl]thio]acetic acid.

7. A compound according to claim 1 which is trans-[[2-[[3-(1,1-dimethylethyl)phenyl]thio]cyclohexyl]thio]acetic acid.

8. A compound according to claim 1 which is trans-[[2-[([1,1'-biphenyl]-3-yl)thio]cyclohexyl]thio]acetic acid.

9. A compound according to claim 1 which is trans-[[2-[[3,5-bis(1,1-dimethylethyl)phenyl]thio]cyclohexyl]oxy]acetic acid.

10. A compound according to claim 1 which is trans-[[2-(phenylthio)cyclohexyl]thio]acetic acid.

11. A pharmaceutical composition for use in inhibiting superoxide generation in a mammal which comprises an amount of a compound of the formula

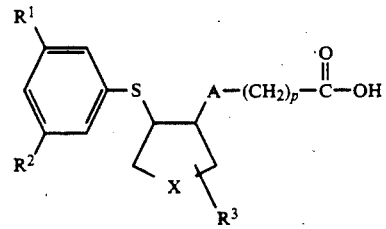

wherein $R^1$ and $R^2$ are the same or different and independently represent tert-alkyl, phenyl, or hydrogen; $R^3$ represents hydrogen or alkyl of 1 to 4 carbon atoms; X represents $(CH_2)_m$ wherein m is 1 or 2; A represents O or $S(O)_n$ wherein n is 0, 1, or 2; and p is an integer from 0 to 4; or a pharmaceutically acceptable salt thereof, which is effective to inhibit superoxide generation, and a pharmaceutically acceptable carrier.

12. A pharmaceutical composition according to claim 11 wherein said compound is selected from the group consisting of
trans-[[2-[[3,5-bis(1,1-dimethylethyl)phenyl]thio]cyclohexyl]thio]acetic acid;
trans-[[2-[[3-(1,1-dimethylethyl)phenyl]thio]cyclohexyl]thio]acetic acid;
trans-[[2-[([1,1'-biphenyl]-3-yl)thio]cyclohexyl] thio]acetic acid;
trans-[[2-[[3,5-bis(1,1-dimethylethyl)phenyl]thio]cyclohexyl]oxy]acetic acid; and
trans-[[2-(phenylthio)cyclohexyl]thio]acetic acid.

13. A pharmaceutical composition for use in stimulating superoxide generation in a mammal which comprises an amount of a compound of the formula

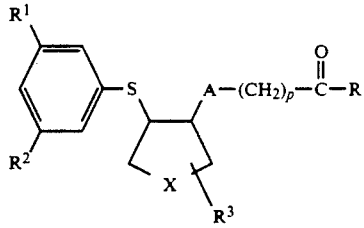

wherein $R^1$ and $R^2$ are the same or different and independently represent tert-alkyl, phenyl, or hydrogen; $R^3$ represents hydrogen or alkyl or 1 to 4 carbon atoms; X represents $(CH_2)_m$ wherein m is 1 or 2; A represents O or $S(O)_n$ wherein n is 0, 1, or 2; p is an integer from 0 to 4; and R represents $OR^4$ wherein $R^4$ is alkyl of 1 to 4 carbon atoms; or $NR^5R^6$ wherein $R^5$ is hydrogen or alkyl, and $R^6$ is hydrogen, alkyl, cycloalkyl, substituted cycloalkyl having one or more substituents selected from the group consisting of alkyl, hydroxy, alkoxy, and halogen, phenyl, substituted phenyl having one or more substituents selected from the group consisting of alkyl, hydroxy, alkoxy, halogen, alkylamino, dialkylamino, phenyl and alkylcarbonyl phenylalkyl, or substituted phenylalkyl wherein the phenyl ring has one or more substituents selected from the group consisting of alkyl, hydroxy, alkoxy, halogen, alkylamino, dialkylamino, phenyl and alkylcarbonyl; or a pharmaceutically acceptable salt thereof, which is effective to stimulate superoxide generation, and a pharmaceutically acceptable carrier.

14. A pharmaceutically composition according to claim 13 wherein said compound is methyl trans-[[2-[[3,5-bis(1,1-dimethylethyl)-phenyl]thio]cyclohexyl]thio]acetate.

15. A method of inhibiting superoxide generation in a mammal which comprises administering to a mammal in need of such treatment an amount of a compound of the formula

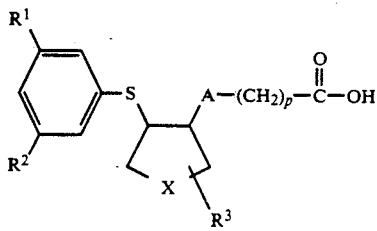

wherein $R^1$ and $R^2$ are the same or different and independently represent tert-alkyl, phenyl, or hydrogen; $R^3$ represents hydrogen or alkyl of 1 to 4 carbon atoms; X represents $(CH_2)_m$ wherein m is 1 or 2; A represents O or $S(O)_n$ wherein n is 0, 1, or 2; and p is an integer from 0 to 4; or a pharmaceutically acceptable salt thereof, which is effective to inhibit superoxide generation.

16. A method according to claim 15 wherein said compound is selected from the group consisting of trans-[[2-[[3,5-bis(1,1-dimethylethyl)phenyl]thio]cyclohexyl]thio]acetic acid;

trans-[[2-[[3-(1,1-dimethylethyl)phenyl]thio]cyclohexyl]thio]acetic acid;

trans-[[2-[([1,1'-biphenyl]-3-yl)thio]cyclohexyl]thio]acetic acid;

trans-[[2-[[3,5-bis(1,1-dimethylethyl)phenyl]thio]cyclohexyl]oxy]acetic acid; and trans-[[2-(phenylthio)cyclohexyl]thio]acetic acid.

17. A method of stimulating superoxide generation in a mammal which comprises administering to a mammal in need of such treatment an amount of a compound of the formula

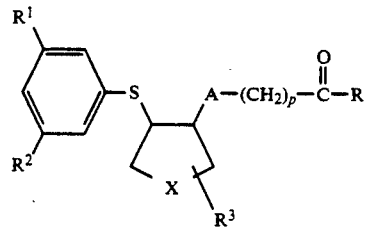

wherein $R^1$ and $R^2$ are the same of different and independently represent tert-alkyl, phenyl, or hydrogen; $R^3$ represents hydrogen or alkyl or 1 to 4 carbon atoms; X represents $(CH_2)_m$ wherein m is 1 or 2; A represents O or $S(O)_n$ wherein n is 0, 1, or 2; p is an integer from 0 to 4; and R represents $OR^4$ wherein $R^4$ is alkyl of 1 to 4 carbon atoms; $NR^5R^6$ wherein $R^5$ is hydrogen or alkyl, and $R^6$ is hydrogen, alkyl, cycloalkyl, substituted cycloalkyl having one or ore substituents selected from the group consisting of alkyl, hydroxy, alkoxy, and halogen, phenyl, substituted phenyl having one or more substituents selected from the group consisting of alkyl, hydroxy, alkoxy, halogen, alkylamino, dialkylamino, phenyl, and alkylcarbonyl, phenylalkyl, or substituted phenylalkyl wherein the phenyl ring has one or more substituents selected from the group consisting of alkyl, hydroxy, alkoxy, halogen, alkylamino, dialkylamino, phenyl, and alkylcarbonyl; or a pharmaceutically acceptable salt thereof, which is effective to stimulate superoxide generation.

18. A method according to claim 17 wherein said compound is methyl trans-[[2-[[3,5-bis(1,1-dimethylethyl)-phenyl]thio]cyclohexyl]thio]acetate.

* * * * *

UNITED STATES PATENT AND TRADEMARK OFFICE
CERTIFICATE OF CORRECTION

PATENT NO. : 5,272,178     Page 1 of 4
DATED : December 21, 1993
INVENTOR(S) : Mueller, et al.

It is certified that error appears in the above-indentified patent and that said Letters Patent is hereby corrected as shown below:

Column 4, line 4, reading "discloses" should read -- disclose --.

Column 6, line 44, reading "$H_2O_2$, OH" should read -- $H_2O_2$, ·OH --.

Column 9, line 37, reading "Such salt" should read -- Such salts --.

Column 17, line 6, reading "an measured" should read -- and measured --.

Column 17, line 48, reading "3.2% $10^{-5}$M" should read -- 3.2% at $10^{-5}$M --.

Column 19, line 36, reading "(m.w. = 22.4):" should read -- (m.w. = 222.4): --.

Column 21, line 25, after "Example 7" should read -- trans-[[2-(phenylthio)cyclohexyl]thio]acetic acid --.

Column 21, line 51, after "Example 8" should read -- O-[3-(1,1-dimethylethyl)phenyl]dimethyl-carbamothioate --.

Column 22, line 8, after "Example 9" should read -- 3-(1,1-dimethylethyl)benzenethiol --.

Column 22, line 22, after "Example 10" should read -- trans-2-[[3-(1,1-dimethylethyl)phenyl]thio]-cyclohexanol --.

UNITED STATES PATENT AND TRADEMARK OFFICE
CERTIFICATE OF CORRECTION

PATENT NO. : 5,272,178
DATED : December 21, 1993
INVENTOR(S) : Mueller, et al.

It is certified that error appears in the above-indentified patent and that said Letters Patent is hereby corrected as shown below:

Column 22, line 35, after "Example 11" should read -- trans-[[2-[[3-(1,1-dimethylethyl)phenyl]thio]-cyclohexyl]thio]acetic acid --.

Column 23, line 2, after "Example 12" should read -- [1,1'-biphenyl]-3-yl dimethylcarbamoate --.

Column 23, line 20, after "Example 13" should read -- 3-[1,1'-biphenyl]thiol --.

Column 23, line 35, after "Example 14" should read -- trans-2-[([1,1'-biphenyl]-3-yl)thio]cyclohexanol --.

Column 23, line 52, after "Example 15" should read -- trans-[[2-[([1,1'-biphenyl]-3-yl)thio]cyclohexyl]-thio]acetic acid --.

Column 24, line 5, after "Example 16" should read -- trans-2-[[2-[[3,5-bis(1,1-dimethylethyl)phenyl]-thio]cyclohexyl]thio]-N-methyl-N-(2-pyridinylethyl)acetamide --.

Column 24, line 32, reading "produce" should read -- product --.

Column 24, line 39, reading "S, 5.45" should read -- S, 5.46 --.

Column 24, line 39, reading "C, 69.96;" should read -- C, 69.95; --.

UNITED STATES PATENT AND TRADEMARK OFFICE
CERTIFICATE OF CORRECTION

PATENT NO. : 5,272,178
DATED : December 21, 1993
INVENTOR(S) : Mueller, et al.

It is certified that error appears in the above-indentified patent and that said Letters Patent is hereby corrected as shown below:

Column 24, line 43, after "Example 17" should read -- trans-[[2-[[3,5-bis(1,1-dimethylethyl)phenyl]-thio]cyclohexyl]oxy]acetic acid --.

Column 25, line 5, after "Example 18" should read -- 3,6-dioxabicyclo[3.1.0]hexane --.

Column 25, line 16, reading "trifuloroacetic" should read -- trifluoroacetic --.

Column 25, line 27, after "Example 19" should read -- trans-4-[[3,5-bis(1,1-dimethylethyl)phenyl]thio]-tetrahydro-3-furanol --.

Column 25, line 52, after "Example 20" should read -- trans-4-[[3,5-bis(1,1-dimethylethyl)phenyl]thio]-tetrahydro-3-furanol, acetate --.

Column 26, line 7, after "Example 21" should read -- butanedioic acid, trans-mono[4-[[3,5-bis(1,1-dimethylethyl)4-hydroxyphenyl]thio]tetrahydro-3-furanyl]-ester --.

Column 27, line 42, reading "NA$^5$SR$^6$" should read -- NR$^5$R$^6$ --.

Column 28, line 54, reading "or 1 to 4" should read -- of 1 to 4 --.

Column 29, line 5, reading "pharmaceutically" should read -- pharmaceutical --.

UNITED STATES PATENT AND TRADEMARK OFFICE
CERTIFICATE OF CORRECTION

PATENT NO. : 5,272,178

DATED : December 21, 1993

INVENTOR(S) : Mueller, et al.

It is certified that error appears in the above-indentified patent and that said Letters Patent is hereby corrected as shown below:

Column 30, line 17, reading "same of" should read -- same or --.

Column 30, line 25, reading "or ore" should read -- or more --.

Signed and Sealed this

Fifth Day of September, 1995

Attest:

BRUCE LEHMAN

Attesting Officer

Commissioner of Patents and Trademarks